United States Patent [19]

Kathawala

[11] 4,031,233

[45] June 21, 1977

[54] PHENOXYPHENYL IMIDAZOLYL METHANOLS AND KETONE DERIVATIVES THEREOF

[75] Inventor: Faizulla G. Kathawala, West Orange, N.J.

[73] Assignee: Sandoz, Inc., E. Hanover, N.J.

[22] Filed: Feb. 9, 1976

[21] Appl. No.: 656,247

[52] U.S. Cl. .............................. 424/273; 260/309
[51] Int. Cl.$^2$ ..................................... C07D 233/64
[58] Field of Search .................... 260/309; 424/273

[56] References Cited

UNITED STATES PATENTS 3,772,315  11/1973  Regel et al. ..................... 260/309

OTHER PUBLICATIONS

Ogawa et al., Chem. Abst. 1972, vol. 77, No. 151168*b*.
Matsui et al., Chem. Abst., vol. 81, No. 63625*a*.
Pinkerton et al., J. Heterocycl. Chem., 1972, vol. 9, pp.67–72.
Roe, J. Chem. Soc., (London), 1963, pp. 2195–2200.

*Primary Examiner*—Natalie Trousof
*Attorney, Agent, or Firm*—Gerald D. Sharkin; Richard E. Vila; Frederick H. Weinfeldt

[57] ABSTRACT

Imidazolyl-phenoxyphenyl-carbinols and ketones, e.g., α-(p-phenoxyphenyl)-1-methyl-2-imidazolylmethanol and p-phenoxyphenyl 1-methyl-2-imidazolyl ketone, are useful as hypolipidemic agents. The ketones are obtainable by oxidation of corresponding imidazolyl-phenoxyphenyl-carbinols.

27 Claims, No Drawings

PHENOXYPHENYL IMIDAZOLYL METHANOLS AND KETONE DERIVATIVES THEREOF

This invention relates to organic compounds, and more particularly to imidazolyl-p-phenoxyphenyl-carbinols and ketones, and (pharmaceutically acceptable acid addition salts thereof) and to pharmaceutical compositions containing such compounds, as well as to use of such compounds as pharmaceuticals.

The compounds of this invention are conveniently represented by the formula (I):

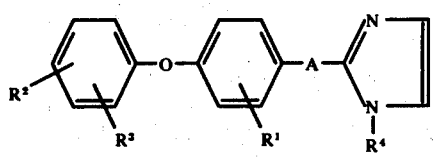

wherein
$R^1$ is, a hydrogen atom, alkyl having from 1 to 4 carbons, or fluoro or chloro, i.e., a halogen atom having an atomic weight of from about 19 to 36;
each of $R^2$ and $R^3$ is, independently, a hydrogen atom, alkyl having from 1 to 4 carbon atoms and fluoro or chloro, i.e., a halogen atom having an atomic weight of from about 19 to 36; or alkoxy having from 1 to 4 carbons; provided that when $R^2$ and $R^3$ are on adjacent carbons they are not both branched alkyl or branched alkoxy;
A is either

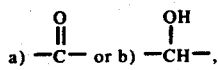

and
$R^4$ is alkyl having from 1 to 18 carbon atoms.

In the above-presented definitions of alkyl and alkoxy groups suitable as $R^1$, $R^2$, $R^3$ or $R^4$ when it has four or less carbon atoms, it is to be understood that the alkyl portions may be methyl, ethyl, propyl or butyl, including isomers where such exist, e.g., t-butyl. When $R^4$ has 5 to 18 carbon atoms, (higher alkyl) it may be branched or unbranched, e.g., n-octyl, n-decyl, n-dodecyl, n-tetradecyl, n-hexadecyl or 3,7,11-trimethyl-n-dodedecyl.

Compounds I, then consists of two classes of compounds, i.e., compounds I$a$ when A is of type (a), i.e., carbonyl:

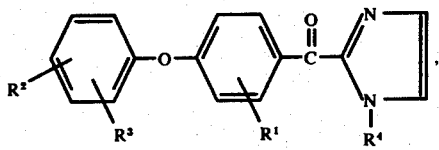

and compounds I$b$ when A is of type (b), i.e., a carbinol function:

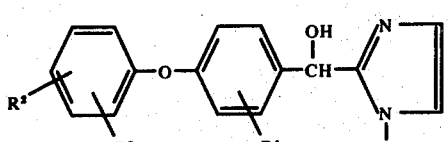

wherein $R^1$, $R^2$, $R^3$ and $R^4$ are as defined above.

Compounds I$a$ may be obtained by oxidizing (process a) on a suitable medium, corresponding compounds I$b$.

The oxidation of a compound I$b$, (process a) may be accomplished in the conventional manner for oxidizing a secondary aliphatic alcohol function to a carbonyl function, e.g., by reacting a compound I$b$, at a temperature of, e.g., from about 20° to 140° C., in the presence of activated manganese dioxide ($MnO_2$) in a suitable medium, i.e., an inert solvent such as dichloromethane, 1,2-dichloroethane, benzene, toluene, xylene or dioxane. Preferably the reaction is carried out at the reflux temperature of the solvent, which is preferably dichloromethane, i.e., $CH_2Cl_2$.

Compounds I$b$ may be obtained by condensing a Grignard agent of formula II

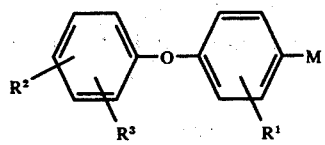

wherein M is magnesium halide and $R^1$, $R^2$ and $R^3$ are as defined above, with a suitable imidazole aldehyde (III):

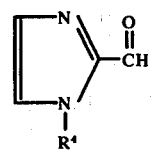

wherein $R^4$ is as defined above, in the presence of an aprotic solvent and under essentially anhydrous conditions, to obtain a corresponding Grignard adduct, which is then hydrolyzed to the corresponding Compound I$b$.

The preparation of a compound I$b$ (process b) is conveniently carried out in the manner, and under the conditions conventionally applied in carrying out the well-known Grignard reactions. Convenient temperatures are those of from about 0° to 70° C., preferably at the reflux temperature of the solvent. Suitable aprotic solvents are ethers, such as tetrahydrofuran and diethyl ether. Magnesium halides include magnesium bromide and iodide; magnesium bromide being preferred as M. It is particularly convenient to prepare a Grignard reagent in which M is a magnesium halide in situ, e.g., by reacting an aryl halide of formula IV;

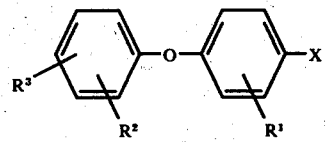

wherein $R^1$, $R^2$ and $R^3$, are as defined above, and X is bromo or iodo, with magnesium metal at temperatures and in a solvent suitable for carrying out (process b), under essentially anhydrous conditions. A small amount of solid iodine may be added to aid in initiating the reaction, as is commonly done in preparing Grignard reagents. Avoidance of moisture to achieve essentially anhydrous conditions is exercised, e.g., "dry" solvents and moisture-free apparatus being employed.

The hydrolysis of the resulting adduct may be carried out in the manner conventionally employed in hydrolyzing Grignard adducts, e.g., by treating the Grignard adduct with water, or an aqueous salt, acid or base, e.g., saturated ammonium chloride solution.

The products of the above-described reactions may be recovered and refined in conventional manner, e.g., by crystallization, distillation or chromatographic techniques, such as eluting from a chromotographic column or separating on a silica layer.

Starting materials and reagents used in the above-described reactions, e.g., compounds III and IV are either known and obtained by methods described in the literature, or where not known, may be obtained by methods analogous to those described in the literature. Some of the reactants and starting materials are commercially available.

The preferred compounds of the formula I are those in which A is

and/or $R^4$ is lower alkyl of 1 to 4 carbon atoms, especially the compounds of the formula I in which A is

and $R^4$ is lower alkyl of 1 to 4 carbon atoms, especially methyl.

The above-described reactions may conveniently be represented by the following reaction scheme wherein $R^1$, $R^2$, $R^3$ and $R^4$ and M are as defined above.

REACTION SCHEME

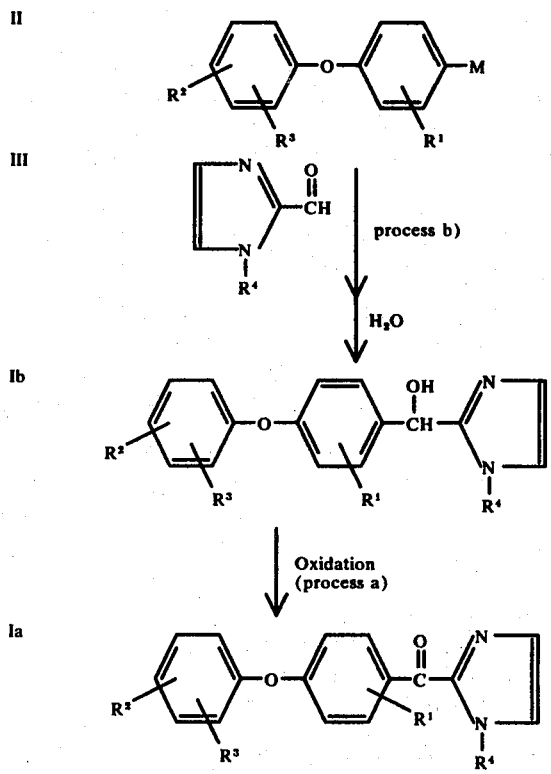

UTILITY STATEMENT

The compounds of formula I are useful because they possess pharmacological activity in animals. In particular, the compounds are useful as hypolipidemic agents in the treatment of lipidemia as indicated by the fall in cholesterol and/or triglyceride levels in male albino Wistar rats weighing 110–130 g. initially. The rats are maintained on drug-free laboratory chow diet for seven days and then divided into groups of 6 to 10 animals. Each group, with the exception of the control, is then given orally 7.5 to 500 milligrams per kilogram of body weight per diem of the test compound for 6 days. At the end of this period, the animals are anesthetized with sodium hexobarbital and bled from the carotid arteries. Serum or plasma samples are collected and 1.0 ml. of the serum is added to 9.0 ml. redistilled isopropanol. Two auto-analyzer cupsful of a mixture of zeolite-copper hydroxide and Lloydds reagent (Kessler, G., and Lederer, H., 1965, Technicon Symposium, Madiad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example from about 20 to 50% of ethanol, and the like, or parenterally in the form of sterile injectable solutions or suspensions containing from about 0.5 to 5% suspending agent in an isotonic medium. These pharmaceutical preparations may contain, for example, from about 0.5 up to about 90% of the active ingredient in combination with the carrier, more usually between 5 and 60% by weight.

Furthermore, the compounds of formula I may be similarly administered in the form of their non-toxic pharmaceutically acceptable acid addition salts. Such salts possess the same order of activity as the free base, are readily prepared by reacting the free base with an appropriate acid and accordingly are included within the scope of the invention. Representative of such salts are the mineral acid salts, such as the hydrochloride, hydrobromide, sulfate, phosphate and the like and the organic acid salts such as the benzoate, acetate, maleate, fumarate, p-toluenesulfonate, benzenesulfonate and the like.

The hypolipidemic effective dosage of active ingredient employed for the treatment of lipidemia may vary depending on the particular compound employed, the mode of administration and the severity of the condition being treated. However, in general, satisfactory results are obtained when the compounds of formula I are administered at a daily dosage of from about 7 milligrams to about 500 milligrams per kilogram of animal body weight, preferably given in divided doses two to four times a day, or in sustained release form. For most large mammals, the total daily dosage is from about 500 milligrams to about 2000 milligrams. Dosage forms suitable for internal use comprise from about 125 to about 1000 milligrams of the active compound in intimate admixture with a solid or liquid pharmaceutically acceptable carrier. Solid carriers include starch, lactose and kaolin, while liquid carriers include polyethylene glycols and edible oils such as corn, peanut and seasame oils, as are appropriate to the nature of the active ingredient and the particular form of administration desired.

Particular embodiments of this invention include those subclasses of compounds I in which the A portion is of type (a) and: $R^1$ is a hydrogen atom; each of $R^1$, $R^2$, and $R^3$ is a hydrogen atom; or $R^4$ is a alkyl having from 1 to 4 carbon atoms, particularly methyl; and compounds I in which the A portion is of type (b) and: $R^1$ is a hydrogen atom; each of $R^1$, $R^2$ and $R^3$ is a hydrogen atom; or $R^4$ is alkyl having from 1 to 4 carbon atoms, particularly methyl (and pharmaceutically acceptable acid addition salts thereof), as well as the use of compounds of such subclasses for the above-described usage.

In the following examples which illustrate the invention, temperatures are in degrees centigrade, and room temperature is 20° to 30° C.

EXAMPLE 1

α-(p-phenoxyphenyl)-1-methyl-2-imidazalylmethanol
*

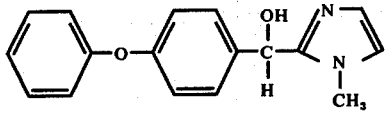

To 2.8 g. of metallic magnesium and a crystal of iodine are added (all at once) 25 ml. of a solution of 24.0 g. 4-bromodiphenylether in 150 ml. absolute tetrahydrofurane(THF) to initiate Grignard reaction. Thereafter the rest of the THF solution of 4-bromodiphenylether is added dropwise to maintain gentle reflux and then refluxed for an additional 30 minutes. The reaction mixture is cooled and to it is added dropwise a solution of 11.0 g. 1-methyl-2-imidazole-carboxaldehyde in 50 ml. absolute THF, and the resulting reaction mixture is stirred at room temperature for 2 hours. The reaction mixture is then poured into 200 ml. saturated ammonium chloride and extracted several times with ether. The combined ether extracts, after washing with distilled water, are dried over anhydrous sodium sulfate, filtered and evaporated under vacuum to dryness. The residue is treated with 6N hydrochloric acid to give the hydrochloride of the title product which is then filtered and washed well with ether. The precipitate of the hydrochloride is then suspended in 2N aqueous sodium hydroxide till basic and extracted several times with ether. The combined ether extracts, after drying over anhydrous sodium sulfate, are filtered, evaporated under vacuum to dryness, and from the residue is crystallized with cold pentane the title product, m.p. 118°-119°.

* may also be called α-(p-phenoxyphenyl)-1-methyl-2-imidazolmethanol; 4-phenoxy-α-(1-methylimidazol-2-yl) benzyl alcohol; 2-(α-hydroxy-p-phenoxybenzyl)-1-methyl-imidazole; or p-phenoxyphenyl-2-(1-methyl)-imidazolylmethanol.

EXAMPLE 2 p-phenoxyphenyl-1-methyl-2-imidazolylketone*

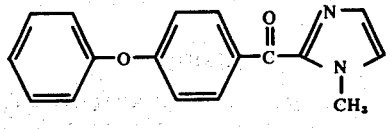

A mixture of 6.0 g. α-(p-phenoxyphenyl)-1-methyl-2-imidazolylmethanol and 8.0 g. of activated manganese dioxide in 200 ml. methylenechloride is refluxed for 12 hours. The reaction mixture is then filtered free of magnesium dioxide and evaporated under vacuum to dryness to give the title product as a viscous oil.

* may also be called (p-phenoxyphenyl)-1-methyl-2-imidazolyl-ketone, or 2-(p-phenoxybenzoyl)-1-methylimidazole.

EXAMPLE 3

Repeating the procedures of Examples 1 and 2, but replacing the 1methyl-2-imidazole carboxaldehyde used in Example 1, with an approximately equivalent amount of 1-(n-tetradecyl)-2-imidazole carboxaldehyde, there is accordingly obtained:

a. α-(p-phenoxyphenyl)-1-(n-tetradecyl)-2-imidazalylmethanol (as an oil); and
b. p-phenoxyphenyl-1-(n-tetradecyl)-2-imidazolylketone (as an oil).

EXAMPLE 4

Following the procedure or Example 1, but using in place of the 4-bromodiphenyl ether used therein; an approximately equivalent amount of:
a. 4-(p-methoxyphenoxy)-bromobenzene;
b. 4-(p-fluoro-phenoxy)-bromobenzene;
c. 1-bromo-4-(p-methoxyphenoxy)-3-chlorobenzene;
d. 4-(p-toloxy)-bromobenzene;
e. 4-(3'-5'-di-tert.-butylphenoxy)-bromobenzene; or
f. 4-(p-chlorophenoxy)-bromobenzene;

there is similarly obtained respectively:
a. α-[4-(p-methoxyphenoxy)-phenyl]-1-methyl-2-imidazolylmethanol;
b. α-[4-(p-fluorophenoxy)-phenyl]-1-methyl-2-imidazolylmethanol;
c. α-[3-chloro-4-(p-methoxyphenoxy)-phenyl]-1methyl-2-imidazolylmethanol;
d. α-[4-(p-toloxy)phenyl]-1-methyl-2-imidazolylmethanol;
e. α-[4-(3', 5'-di-tert.-butylphenoxy)-phenyl]-1-methyl-2-imidazolylmethanol; and
f. α-[4-(p-chlorophenoxy)-phenyl]-1-methyl-2-imidazolylmethanol

EXAMPLE 5

The following procedure of Example 2, but using the place of the α-(p-phenoxyphenyl)-1-methyl-2-imidazolyl-methanol used therein, an approximately equivalent amount of each of the products of Example 4, there is accordingly, obtained, respectively:
a. [4-(p-methoxyphenoxy)-phenyl]1-methyl-2-imidazolyl-ketone;
b. [4-(p-fluorophenoxy)-phenyl]1-methyl-2-imidazolylketone;
c. [3-chloro-4-(p-methoxyphenoxy)-phenyl]1-methyl-2-imidazolylketone;

d. [4-(p-toloxy)phenyl]1-methyl-2-imidazolylketone
e. [4-(3', 5'-di-tert.-butylphenoxy)phenyl]1-methyl-2-imidazolylketone; and
f. [4-(p-chlorophenoxy)-phenyl]1-methyl-2-imidazolylketone.

EXAMPLE 6

Tablets and capsules containing the ingredients indicated below may be prepared by conventional techniques and are useful in treating lipidemia in mammals at a dose of one tablet or capsule 2 to 4 times per day:

| Ingredient | Weight (in mg.) Tablet | Capsule |
|---|---|---|
| α-(p-phenoxyphenyl)-1-methyl-2-imidazolylmethanol | 150 | 150 |
| Tragacanth | 10 | |
| Lactose | 97.5 | 150 |
| Corn Starch | 25 | |
| Talcum | 15 | |
| Magnesium Stearate | 2.5 | |

What is claimed is:
1. A compound which is a member of the group consisting of a free organic base of the formula

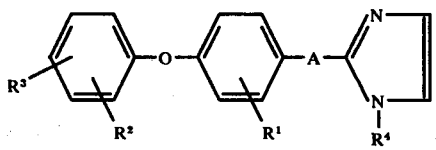

wherein
$R^1$ is a hydrogen atom, alkyl having from 1 to 4 carbon atoms, fluoro or chloro;
$R^2$ is a hydrogen atom, alkyl having from 1 to 4 carbon atoms, or alkoxy having from 1 to 4 carbon atoms, fluoro or chloro;
$R^3$ is a hydrogen atom, alkyl having from 1 to 4 carbon atoms, or alkoxy having from 1 to 4 carbon atoms, fluoro or chloro;
$R^4$ is alkyl having from 1 to 18 carbon atoms; and
A is either

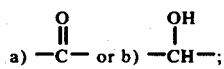

and a
pharmaceutically acceptable acid addition salt thereof; provided that when $R^2$ and $R^3$ are on adjacent carbons they are not both alkyl or alkoxy which are branched.

2. A compound of claim 1 in which A is of type (a)
3. A compound of claim 2 in which $R^1$ is a hydrogen atom.
4. A compound of claim 3 in which each of $R^2$ and $R^3$ is a hydrogen atom.
5. The compound of claim 4 which is p-phenoxyphenyl-1-methyl-2-imidazolylketone.
6. The compound of claim 4 which is p-phenoxyphenyl-1-(n-tetradecyl)-2-imidazolylketone.
7. A compound of claim 1 in which A is of type (b).
8. A compound of claim 7 in which $R^1$ is a hydrogen atom.
9. A compound of claim 8 in which each of $R^2$ and $R^3$ is a hydrogen atom.

10. The compound of claim 9 which is α-(p-phenoxyphenyl)-1-methyl-2-imidazolylmethanol.
11. The compound of claim 9 which is α-(p-phenoxyphenyl)-1-(n-tetradecyl)-2-imidazolylmethanol.
12. A compound of claim 2 in which $R^4$ is alkyl of 1 to 4 carbon atoms.
13. A compound of claim 12 in which $R^4$ is methyl.
14. A compound of claim 7 in which $R^4$ is alkyl of 1 to 4 carbon atoms.
15. A compound of claim 14 in which $R^4$ is methyl.
16. A pharmaceutical composition useful in reducing the blood level of lipid materials in a mammal, comprising a pharmaceutically-acceptable carrier and, in an amount effective in reducing the level of lipid materials in the blood of said mammal, a compound which is a member of the group consisting of a free organic base of the formula

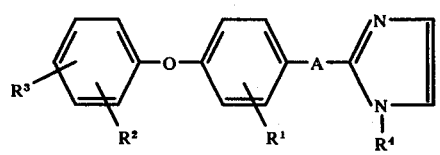

wherein
$R^1$ is a hydrogen atom, alkyl having from 1 to 4 carbon atoms, fluoro or chloro;
$R^2$ is a hydrogen atom, alkyl having from 1 to 4 carbon atoms, or alkoxy having from 1 to 4 carbon atoms, fluoro or chloro;
$R^3$ is a hydrogen atom, alkyl having from 1 to 4 carbon atoms, or alkoxy having from 1 to 4 carbon atoms, fluoro or chloro;
$R^4$ is alkyl having from 1 to 18 carbon atoms; and
A is either

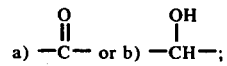

and a
pharmaceutically acceptable acid addition salt thereof; provided that when $R^2$ and $R^3$ are on adjacent carbons they are not both alkyl or alkoxy which are branched.

17. A composition of claim 16, in unit dosage form, in which the compound is present in an amount of from about 125 to about 1000 milligrams.
18. A composition of claim 16 in which the compound is α-(p-phenoxyphenyl)-1-methyl-2-imidazolylmethanol.
19. A method of reducing the blood level of lipid materials in a mammal, comprising administering to said mammal, in an amount effective in reducing the blood level of lipid materials of said mammal, a compound which is a member of the group consisting of a free organic base of the formula

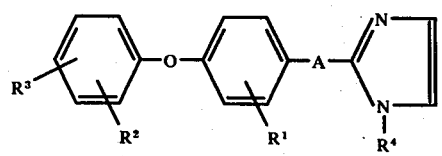

wherein
$R^1$ is a hydrogen atom, alkyl having from 1 to 4 carbon atoms, fluoro or chloro;

$R^2$ is a hydrogen atom, alkyl having from 1 to 4 carbon atoms, or alkoxy having from 1 to 4 carbon atoms, fluoro or chloro;

$R^3$ is a hydrogen atom, alkyl having from 1 to 4 carbon atoms, or alkoxy having from 1 to 4 carbon atoms, fluoro or chloro;

$R^4$ is alkyl having from 1 to 18 carbon atoms; and

A is either

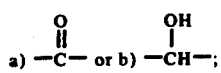

a) $-\overset{\overset{O}{\|}}{C}-$ or b) $-\overset{\overset{OH}{|}}{CH}-$;

and a pharmaceutically acceptable acid addition salt thereof; provided that when $R^2$ and $R^3$ are on adjacent carbons they are not both alkyl or alkoxy which are branched.

20. A method of claim 19 in which the compound is administered in a total daily dosage of from about 500 to 2000 milligrams.

21. The method of claim 19 in which the A portion of the compound is of type (a).

22. The method of claim 21 in which the $R^4$ portion of the compound is alkyl of from 1 to 4 carbon atoms.

23. The method of claim 22 in which $R^4$ is methyl.

24. The method of claim 19 in which the A portion of the compound is of type (b).

25. The method of claim 24, in which the $R^4$ portion of the compound is alkyl of from 1 to 4 carbon atoms.

26. The method of claim 25 in which $R^4$ is methyl.

27. The method of claim 26 in which the compound is α-(p-phenoxyphenyl)-1-methyl-2-imidazolylmethanol.

* * * * *